United States Patent [19]

Oshlack et al.

[11] Patent Number: 5,266,331

[45] Date of Patent: * Nov. 30, 1993

[54] CONTROLLED RELEASE OXYCODONE COMPOSITIONS

[75] Inventors: Benjamin Oshlack, New York; John J. Minogue, Mount Vernon, both of N.Y.; Mark Chasin, Manalpan, N.J.

[73] Assignee: Euroceltique, S.A., Luxembourg

[*] Notice: The portion of the term of this patent subsequent to Feb. 5, 2008 has been disclaimed.

[21] Appl. No.: 800,549

[22] Filed: Nov. 27, 1991

[51] Int. Cl.$^5$ .......................... A61K 9/22; A61K 9/26
[52] U.S. Cl. ..................................... 424/468; 424/469; 424/470; 424/486; 424/487; 424/488; 424/494; 424/496; 424/497; 424/498; 424/501; 424/502; 424/495
[58] Field of Search ............... 424/464, 465, 468, 469, 424/470, 486, 487, 488, 494, 496, 497, 498

[56] References Cited

U.S. PATENT DOCUMENTS 4,861,598  8/1989  Oshlack ..................... 424/470
4,990,341  2/1991  Goldie et al. ................. 424/484

Primary Examiner—Thurman K. Page
Assistant Examiner—James M. Spear
Attorney, Agent, or Firm—Steinberg & Raskin

[57] ABSTRACT

A solid controlled release, oral dosage form, the dosage form comprising a therapeutically effective amount of oxycodone or a salt thereof in a matrix wherein the dissolution rate in vitro of the dosage form, when measured by the USP Paddle Method of 100 rpm in 900 ml aqueous buffer (pH between 1.6 and 7.2) at 37° C. is between 12.5% and 42.5% (by weight) oxycodone released after 1 hour, between 25% and 55% (by weight) oxycodone released after 2 hours, between 45% and 75% (by weight) oxycodone released after 4 hours and between 55% and 85% (by weight) oxycodone released after 6 hours, the in vitro release rate being independent of pH between pH 1.6 and 7.2 and chosen such that the peak plasma level of oxycodone obtained in vivo occurs between 2 and 4 hours after administration of the dosage form.

17 Claims, No Drawings

CONTROLLED RELEASE OXYCODONE COMPOSITIONS

BACKGROUND OF THE INVENTION

The present invention relates to a solid, controlled release oral dosage form for use in the treatment of moderate to severe pain.

It has previously been known in the art that controlled release compositions of hydromorphone or salts thereof could be prepared in a suitable matrix. For example, U.S. Pat. No. 4,990,341 (Goldie), also assigned to the assignee of the present invention, describes hydromorphone compositions wherein the dissolution rate in vitro of the dosage form, when measured by the USP Paddle Method at 100 rpm in 900 ml aqueous buffer (pH between 1.6 and 7.2) at 37° C., is between 12.5 and 42.5% (by wt) hydromorphone released after 1 hour, between 25 and 55% (by wt) released after 2 hours, between 45 and 75% (by wt) released after 4 hours and between 55 and 85% (by wt) released after 6 hours.

For example, this patent teaches that controlled release hydromorphone compositions can be prepared by incorporating the drug into a controlled release matrix (e.g. hydrophobic polymers, digestible long chain hydrocarbons, polyalkylene glycols), or by incorporating the drug into a normal release matrix and utilizing a coating that controls the release of the drug (e.g. a film coating comprising a wax, shellac or zein, a water insoluble cellulose, a polymethacrylate). In a particularly preferred embodiment, film coated spheroids of hydromorphone and microcrystalline cellulose are film-coated to obtain the desired controlled release of the hydromorphone.

While controlled release compositions utilizing hydromorphone as the therapeutically active ingredient were obtained, controlled release compositions containing other therapeutically active agents having the same medicinal use (analgesia) and structurally related to hydromorphone, such as oxycodone, were not believed to be obtained when using similar techniques as those set forth in U.S Patent No. 4,990,341.

It has now been surprisingly discovered that controlled release compositions which include an analgesic other than hydromorphone are indeed obtainable via the methods set forth in U.S. Pat. No. 4,990,341.

SUMMARY OF THE INVENTION

According to the present invention there is provided a solid, controlled release, oral dosage form, the dosage form comprising a therapeutically effective amount of oxycodone or a salt thereof in a matrix wherein the dissolution rate in vitro of the dosage form, when measured by the USP Paddle Method at 100 rpm in 900 ml aqueous buffer (pH between 1.6 and 7.2) at 37° C. is between 12.5 and 42.5% (by wt) oxycodone released after 1 hour, between 25 and 56% (by wt) oxycodone released after 2 hours, between 45 and 75% (by wt) oxycodone released after 4 hours and between 55 and 85% (by wt) oxycodone released after 6 hours, the in vitro release rate being independent of pH between pH 1.6 and 7.2 and such that the peak plasma level of oxycodone obtained in vivo occurs between 2 and 4 hours after administration of the dosage form.

Preferably, the dosage form contains an analgesically effective amount of oxycodone or a salt thereof. However, other related analgesically effective agents may also be used, including hydromorphone, dihydrocodeine, codeine, dihydromorphine, morphine, buprenorphine, salts thereof, and the like.

USP Paddle Method is the Paddle Method described, e.g., in U.S. Pharmacopoeia XXII (1990).

In the present specification, "independent of pH" means that the difference, at any given time, between the amount of oxycodone released at pH 1.6 and the amount released at any other pH up to, and including, pH 7.2 (when measured in vitro using the USP Paddle Method at 100 rpm in 900 ml aqueous buffer) is 10% (by weight) or less. The amounts released being, in all cases, a mean of at least three experiments.

DETAILED DESCRIPTION

In order to obtain a controlled release drug dosage form having at least a 12 hour therapeutic effect, it is usual in the pharmaceutical art to produce a formulation that gives a peak plasma level of the drug between about 4–8 hours after administration (in a single dose study). The present inventors have surprisingly found that, in the case of oxycodone, a peak plasma level at between 2–4 hours after administration gives at least 12 hours pain relief and, most surprisingly, that the pain relief obtained with such a formulation is greater than that achieved with formulations giving peak plasma levels (of oxycodone) in the normal period of 1–2 hours after administration.

Furthermore, in the case of the present dosage form, therapeutic levels are generally achieved without concurrent side effects, such as nausea, vomiting, constipation and drowsiness, which are often associated with high blood levels of oxycodone. There is also evidence to suggest that the use of the present dosage forms leads to a reduced risk of drug addiction.

A further advantage of the present composition, which releases oxycodone at a rate that is independent of pH between 1.6 and 7.2, is that it avoids dose dumping upon oral administration. In other words, the oxycodone is released evenly throughout the gastrointestinal tract.

The present oral dosage form may be presented as, for example, granules, spheroids or pellets in a capsule or in any other suitable solid form. Preferably, however, the oral dosage form is a tablet.

The present oral dosage form preferably contains between 1 and 50 mg, most especially between 10 and 30 mg, of oxycodone hydrochloride. Alternatively the dosage form may contain molar equivalent amounts of other oxycodone salts or of the oxycodone base.

The present matrix may be any matrix that affords in vitro dissolution rates of oxycodone within the narrow ranges required and that releases the oxycodone in a pH independent manner. Preferably the matrix is a controlled release matrix, although normal release matrices having a coating that controls the release of the drug may be used. Suitable materials for inclusion in a controlled release matrix are (a) Hydrophilic polymers, such as gums, cellulose ethers, acrylic resins and protein derived materials. Of these polymers, the cellulose ethers, especially hydroxyalkylcelluloses and carboxyalkylcelluloses, are preferred. The oral dosage form may contain between 1% and 80% (by weight) of at least one hydrophilic or hydrophobic polymer.

(b) Digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes. Hydrocarbons having a melting point of between 25° and 90° C. are preferred. Of these long chain hydrocarbon materials, fatty (aliphatc) alcohols are preferred. The oral dosage form may contain up to 60% (by weight) of at least one digestible, long chain hydrocarbon.

(c) Polyalkylene glycols. The oral dosage form may contain up to 60% (by weight) of at least one polyalkylene glycol.

One particular suitable matrix comprises at least one water soluble hydroxyalkyl cellulose, at least one $C_{12}$–$C_{36}$, preferably $C_{14}$–$C_{22}$, aliphatic alcohol and, optionally, at least one polyalkylene glycol.

The at least one hydroxyalkyl cellulose is preferably a hydroxy ($C_1$ to $C_6$) alkyl cellulose, such as hydroxypropylcellulose, hydroxypropylmethylcellulose and, especially, hydroxyethyl cellulose. The amount of the at least one hydroxyalkyl cellulose in the present oral dosage form will be determined, inter alia, by the precise rate of oxycodone release required. Preferably however, the oral dosage form contains between 5% and 25%, especially between 6.25% and 15%. (by wt) of the at least one hydroxyalkyl cellulose.

The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of oxycodone release required. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In a preferred embodiment, the controlled release composition comprises from about 5 to about 25% acrylic resin and from about 8 to about 40% by weight aliphatic alcohol by weight of the total dosage form. A particularly preferred acrylic resin comprises Eudragit TM RS PM commercially available from Rohm Pharma.

In the present preferred dosage form, the ratio of, e.g., the at least one hydroxyalkyl cellulose or acrylic resin to the at least one aliphatic alcohol/ polyalkylene glycol determines, to a considerable extent, the release rate of the oxycodone from the formulation. A ratio of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferred between 1000 and 15000 especially between 1500 and 12000.

Another suitable controlled release matrix would comprise an alkylcellulose (especially ethyl cellulose), a $C_{12}$ to $C_{36}$ aliphatic alcohol and, optionally, a polyalkylene glycol.

In addition to the above ingredients, a controlled release matrix may also contain suitable quantities of other materials, e.g. diluents, lubricants, binders, granulating aids, colorants, flavorants and glidants that are conventional in the pharmaceutical art.

As an alternative to a controlled release matrix, the present matrix may be a normal release matrix having a coat that controls the release of the drug. In particularly preferred embodiments of this aspect of the invention, the present dosage form comprises film coated spheroids containing active ingredient and a non-water soluble spheronising agent. The term spheroid is known in the pharmaceutical art and means a spherical granule having a diameter of between 0.5 mm and 2.5 mm especially between 0.5 mm and 2 mm.

The spheronising agent may be any pharmaceutically acceptable material that, together with the active ingredient, can be spheronised to form spheroids. Microcrystalline cellulose is preferred.

A suitable microcrystalline cellulose is, for example, the material sold as Avicel PH 101 (Trade Mark, FMC Corporation). According to a preferred aspect of the present invention, the film coated spheroids contain between 70% and 99% (by wt), especially between 80% and 95% (by wt), of the spheronising agent, especially microcrystalline cellulose.

In addition to the active ingredient and spheronising agent, the spheroids may also contain a binder. Suitable binders, such as low viscosity, water soluble polymers, will be well known to those skilled in the pharmaceutical art. However, water soluble hydroxy lower alkyl cellulose, such as hydroxy propyl cellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose.

The spheroids are preferably film coated with a material that permits release of the oxycodone (or salt) at a controlled rate in an aqueous medium. The film coat is chosen so as to achieve, in combination with the other ingredients, the in-vitro release rate outlined above (between 12.5% and 42.5% (by wt) release after 1 hour, etc.).

The film coat will generally include a water insoluble material such as
 (a) a wax, either alone or in admixture with a fatty alcohol,
 (b) shellac or zein,
 (c) a water insoluble cellulose, especially ethyl cellulose,
 (d) a polymethacrylate, especially Eudragit ®.

Preferably, the film coat comprises a mixture of the water insoluble material and a water soluble material. The ratio of water insoluble to water soluble material is determined by, amongst other factors, the release rate required and the solubility characteristics of the materials selected.

The water soluble material may be, for example, polyvinylpyrrolidone or, which is preferred, a water soluble cellulose, especially hydroxypropylmethyl cellulose.

Suitable combinations of water insoluble and water soluble materials for the film coat include shellac and polyvinylpyrrolidone or, which is preferred, ethyl cellulose and hydroxypropylmethyl cellulose.

In order to facilitate the preparation of a solid, controlled release, oral dosage form according to this invention there is provided, in a further aspect of the present invention, a process for the preparation of a solid, controlled release, oral dosage form according to the present invention comprising incorporating oxycodone or a salt thereof in a controlled release matrix. Incorporation in the matrix may be effected, for example, by (a) forming granules comprising at least one water soluble hydroxyalkyl cellulose and oxycodone or a oxycodone salt, (b) mixing the hydroxyalkyl cellulose containing granules with at least one $C_{12}$-$C_{36}$ aliphatic alcohol, and (c) optionally, compressing and shaping the granules. Preferably, the granules are formed by wet granulating the hydroxyalkyl cellulose/oxycodone with water. In a particularly preferred embodiment of this process, the amount of water added during the wet granulation step is preferably between 1.5 and 5 times, especially between 1.75 and 3.5 times, the dry weight of the oxycodone.

The present solid, controlled release, oral dosage form may also be prepared, in the form of film coated spheroids, by (a) blending a mixture comprising oxycodone or a oxycodone salt and a non-water soluble spheronising agent, (b) extruding the blended mixture to give an extrudate, (c) spheronising the extrudate until spheroids are formed, and (d) coating the spheroids with a film coat.

The present solid, controlled release, oral dosage form and processes for its preparation will now be described by way of example only.

DETAILED DESCRIPTION OF THE PREFERRED EMBODIMENTS

The following examples illustrate various aspects of the present invention. They are not meant to be construed to limit the claims in any manner whatsoever.

EXAMPLE 1

Controlled Release Oxycodone HCl 30 mg Tablets
Aqueous Manufacture

The required quantities of oxycodone hydrochloride, spray-dried lactose, and Eudragit TM RS PM are transferred into an appropriate-size mixer, and mixed for approximately 5 minutes. While the powders are mixing, the mixture is granulated with enough water to produce a moist granular mass. The granules are then dried in a fluid bed dryer at 60° C., and then passed through an 8-mesh screen. Thereafter, the granules are redried and pushed through a 12-mesh screen. The required quantity of stearyl alcohol is melted at approximately 60°-70° C., and while the granules are mixing, the melted stearyl alcohol is added. The warm granules are returned to the mixer.

The coated granules are removed from the mixer and allowed to cool. The granules are then passed through a 12-mesh screen. The granulate is then lubricated by mixing the required quantity of talc and magnesium stearate in a suitable blender. Tablets are compressed to 375 mg in weight on a suitable tabletting machine. The formula for the tablets of Example 1 is set forth in Table 1 below:

TABLE 1

Formula of Oxycodone HCl 30-mg Tablets

| Component | mg/Tablet | percent (by wt) |
|---|---|---|
| Oxycodone Hydrochloride | 30.0 | 8 |
| Lactose (spray-dried) | 213.75 | 57 |
| Eudragit ® RS PM | 45.0 | 12 |
| Purified Water | q.s.* | — |
| Stearyl Alcohol | 75.0 | 20 |
| Talc | 7.5 | 2 |
| Magnesium Stearate | 3.75 | 1 |
| Total: | 375.0 | 100 |

*Used in manufacture and remains in final product as residual quantity only.

The tablets of Example 1 are then tested for dissolution via the USP Basket Method, 37° C., 100 RPM, first hour 700 ml gastric fluid at pH 1.2, then changed to 900 ml at 7.5. The results are set forth in Table 2 below:

TABLE 2

Dissolution of Oxycodone 30 mg Controlled Release Tablets

| Time | % Oxycodone Dissolved |
|---|---|
| 1 | 33.1 |
| 2 | 43.5 |
| 4 | 58.2 |
| 8 | 73.2 |
| 12 | 81.8 |
| 18 | 85.8 |
| 24 | 89.2 |

EXAMPLE 2

Controlled Oxycodone HCl 10 mg Release Tablets
—Organic Manufacture

The required quantities of oxycodone hydrochloride and spray dried lactose are transferred into an appropriate sized mixer and mix for approximately 6 minutes. Approximately 40 percent of the required Eudragit ® RS PM powder is dispersed in Ethanol. While the powders are mixing, the powders are granulated with the dispersion and the mixing continued until a moist granular mass is formed. Additional ethanol is added if needed to reach granulation end point. The granulation is transferred to a fluid bed dryer and dried at 30° C.; and then passed through a 12-mesh screen. The remaining Eudragit ® RS PM is dispersed in a solvent of 90 parts ethanol and 10 parts purified water; and sprayed onto the granules in the fluid bed granulator/dryer at 30° C. Next, the granulate is passed through a 12-mesh screen. The required quantity of stearyl alcohol is melted at approximately 60°-70° C. The warm granules are returned to the mixer. While mixing, the melted stearyl alcohol is added. The coated granules are removed from the mixer and allowed to cool. Thereafter, they are passed through a 12-mesh screen.

Next, the granulate is lubricated by mixing the required quantities of talc and magnesium stearate in a suitable blender. The granulate is then compressed to 125 mg tablets on a suitable tabletting machine.

The formula for the tablets of Example 2 is set forth in Table 3 below:

TABLE 3

Formula of Oxycodone HCl 10 mg Controlled Release Tablets

| Component | Mg/Tablet | Percent (by wt) |
|---|---|---|
| Oxycodone hydrochloride | 10.00 | 8 |
| Lactose (spray-dried) | 71.25 | 57 |
| Eudragit ® RS PM | 15.00 | 12 |
| Ethanol | q.s.* | — |

TABLE 3-continued

Formula of Oxycodone HCl 10 mg Controlled Release Tablets

| Component | Mg/Tablet | Percent (by wt) |
|---|---|---|
| Purified Water | q.s.* | — |
| Stearyl Alcohol | 25.00 | 20 |
| Talc | 2.50 | 2 |
| Magnesium stearate | 1.25 | 1 |
| Total: | 125.00 mg | 100 |

*Used only in the manufacture and remains in final product as residual quantity only.

The tablets of Example 2 are then tested for dissolution via USP Basket Method at 37° C., 100 RPM, first hour 700 ml simulated gastric (pH 1.2) then changed to 900 ml at pH 7.5. The results are set forth in Table 4 below:

TABLE 4

Dissolution of Oxycodone 10 mg Controlled Release Tablets

| Hour | % Dissolved |
|---|---|
| 1 | 35.9 |
| 2 | 47.7 |
| 4 | 58.5 |
| 8 | 67.7 |
| 12 | 74.5 |
| 18 | 76.9 |
| 24 | 81.2 |

EXAMPLE 3

Controlled Release Oxycodone 10 mg Tablets (Aqueous Manufacture)

Eudragit ® RS 30D and Triacetin ® are combined while passing though a 60 mesh screen, and mixed under low shear for approximately 5 minutes or until a uniform dispersion is observed.

Next, suitable quantities of Oxycodone HCl, lactose, and povidone are placed into a fluid bed granulator/dryer (FBD) bowl, and the suspension sprayed onto the powder in the fluid bed. After spraying, the granulation is passed through a #12 screen if necessary to reduce lumps. The dry granulation is placed in a mixer.

In the meantime, the required amount of stearyl alcohol is melted at a temperature of approximately 70° C. The melted stearyl alcohol is incorporated into the granulation while mixing. The waxed granulation is transferred to a fluid bed granulator/dryer or trays and allowed to cool to room temperature or below. The cooled granulation is then passed through a #12 screen. Thereafter, the waxed granulation is placed in a mixer/blender and lubricated with the required amounts of talc and magnesium stearate for approximately 3 minutes, and then the granulate is compressed into 125 mg tablets on a suitable tabletting machine.

The formula for the tablets of Example is set forth in Table 5 below:

TABLE 5

Formula of Controlled Release Oxycodone 10 mg Tablets

| Component | Mg/Tablet | percent (by wt) |
|---|---|---|
| Oxycodone Hydrochloride | 10.0 | 8.0 |
| Lactose (spray dried) | 69.25 | 55.4 |
| Povidone | 5.0 | 4.0 |
| Eudragit ® RS 30D (solids) | 10.0* | 8.0 |
| Triacetin ® | 2.0 | 1.6 |
| Stearyl Alcohol | 25.0 | 20.0 |
| Talc | 2.5 | 2.0 |
| Magnesium Stearate | 1.25 | 1.0 |

TABLE 5-continued

Formula of Controlled Release Oxycodone 10 mg Tablets

| Component | Mg/Tablet | percent (by wt) |
|---|---|---|
| Total: | 125.0 | 100.0 |

*Approximately 33.33 mg Eudragit ® RS 30D Aqueous dispersion is equivalent to 10 mg of Eudragit ® RS 30D dry substance.

The tablets of Example 3 are then tested for dissolution via the USP Basket Method at 37° C., 100 RPM, first hour 700ml simulated gastric fluid at pH 1.2, then changed to 900ml at pH 7.5.

TABLE 6

Dissolution of Oxycodone 10 mg Controlled Release Tablets

| Hour | % Oxycodone Dissolved |
|---|---|
| 1 | 38.0 |
| 2 | 47.5 |
| 4 | 62.0 |
| 8 | 79.8 |
| 12 | 91.1 |
| 18 | 94.9 |
| 24 | 98.7 |

EXAMPLES 4-5

In Example 4, 30 mg controlled release oxycodone hydrochloride tablets are prepared according to the process set forth in Example 1.

In Example 5, 10 mg controlled release oxycodone hydrochloride tablets are prepared according to the process set forth in Example 2.

Thereafter, dissolution studies of the tablets of Examples 4 and 5 are conducted at different pH levels, namely, pH 1.3, 4.56, 6.88 and 7.5.

The results are provided in Tables 7 and 8 below:

TABLE 7

Example 4 Percentage Oxycodone HCl 30 mg Tablets Dissolved Over Time

| pH | 1 | 2 | 4 | 8 | 12 | 18 | 24 |
|---|---|---|---|---|---|---|---|
| 1.3 | 29.5 | 43.7 | 61.8 | 78.9 | 91.0 | 97.0 | 97.1 |
| 4.56 | 34.4 | 49.1 | 66.4 | 82.0 | 95.6 | 99.4 | 101.1 |
| 6.88 | 33.8 | 47.1 | 64.4 | 81.9 | 92.8 | 100.5 | 105.0 |
| 7.5 | 27.0 | 38.6 | 53.5 | 70.0 | 81.8 | 89.7 | 96.6 |

TABLE 8

Example 5 Percentage Oxycodone HCl - 10 mg Tablets Dissolved Over Time

| pH | 1 | 2 | 4 | 8 | 12 | 18 | 24 |
|---|---|---|---|---|---|---|---|
| 1.3 | 25.9 | 41.5 | 58.5 | 73.5 | 85.3 | 90.7 | 94.2 |
| 4.56 | 37.8 | 44.2 | 59.4 | 78.6 | 88.2 | 91.2 | 93.7 |
| 6.88 | 34.7 | 45.2 | 60.0 | 75.5 | 81.4 | 90.3 | 93.9 |
| 7.5 | 33.2 | 40.1 | 51.5 | 66.3 | 75.2 | 81.7 | 86.8 |

EXAMPLES 6-11

In examples 6-11, 4 mg and 10 mg oxycodone Hcl tablets were prepared according to the formulations and methods set forth in the assignee's U.S. Pat. No. 4,844,909.

In Example 6, oxycodone hydrochloride (10.00 gm) was wet granulated with lactose monohydrate (417.5 gm) and hydroxyethyl cellulose (100.00 gm), and the granules were sieved through a 12 mesh screen. The granules were then dried in a fluid bed dryer at 50° C. and sieved through a 16 mesh screen.

Molten cetostearyl alcohol (300.0 gm) was added to the warmed oxycodone containing granules, and the whole was mixed thoroughly. The mixture was allowed to cool in the air, regranulated and sieved through a 16 mesh screen.

Purified Talc (15.0 gm) and magnesium stearate (7.5 gm) were then added and mixed with the granules. The granules were then compressed into tablets.

Example 7 is prepared in the same manner as Example 6; however, the formulation includes 10 mg oxycodone HCl/tablet. The formulas for Examples 6 and 7 are set forth in Tables 9 and 10, respectively.

TABLE 9

| Formulation of Example 6 | | |
|---|---|---|
| Ingredient | mg/tablet | g/batch |
| Oxycodone hydrochloride | 4.0 | 10.0 |
| Lactose monohydrate | 167.0 | 417.5 |
| Hydroxyethylcellulose | 40.0 | 100.0 |
| Cetostearyl alcohol | 120.0 | 300.0 |
| Purified talc | 6.0 | 15.0 |
| Magnesium stearate | 3.0 | 7.5 |

TABLE 10

| Formulation of Example 7 | | |
|---|---|---|
| Ingredient | mg/tablet | g/batch |
| Oxycodone hydrochloride | 10.0 | 25.0 |
| Lactose monohydrate | 167.0 | 417.5 |
| Hydroxyethylcellulose | 40.0 | 100.0 |
| Cetostearyl alcohol | 120.0 | 300.0 |
| Talc | 6.0 | 15.0 |
| Magnesium stearate | 3.0 | 7.5 |

In Example 8, 4 mg oxycodone HCl controlled release tablets are prepared according to the excipient formula cited in Example 2 of U.S. Pat. No. 4,844,909. The method of manufacture is the same as set forth in Examples 6 and 7 above. Example 9 is prepared according to Example 8, except that 10 mg oxycodone HCl is included per tablet. The formulas for Examples 8 and 9 are set forth in Tables 11 and 12, respectively.

TABLE 11

| Formulation of Example 9 | | |
|---|---|---|
| Ingredient | mg/tablet | g/batch |
| Oxycodone hydrochloride | 4.0 | 10.0 |
| Anhydrous Lactose | 167.0 | 417.5 |
| Hydroxyethylcellulose | 30.0 | 75.0 |
| Cetostearyl alcohol | 90.0 | 225.0 |
| Talc | 6.0 | 15.0 |
| Magnesium stearate | 3.0 | 7.5 |

TABLE 12

| Formulation of Example 9 | | |
|---|---|---|
| Ingredient | mg/tablet | g/batch |
| Oxycodone hydrochloride | 10.0 | 25.0 |
| Hydrous lactose | 167.0 | 417.5 |
| Hydroxyethylcellulose | 30.0 | 75.0 |
| Cetostearyl alcohol | 90.0 | 225.0 |
| Talc | 6.0 | 15.0 |
| Magnesium stearate | 3.0 | 7.5 |

In Example 10, oxycodone 4 mg controlled release tablets are prepared with the same excipient formula cited in Example 3 of U.S. Pat. No. 4,844,909.

Oxycodone hydrochloride (32.0 gm) was wet granulated with lactose monohydrate (240.0 gm) hydroxyethyl cellulose (80.0 gm) and methacrylic acid copolymer (240.0 gm, Eudragit ® L-100-55), and the granules were sieved through a 12 mesh screen. The granules were then dried in a Fluid Bed Dryer at 50° C. and passed through a 16 mesh screen.

The warmed oxycodone containing granules was added molten cetostearyl alcohol (240.0 gm), and the whole was mixed thoroughly. The mixture was allowed to cool in the air, regranulated and sieved through a 16 mesh screen. The granules were then compressed into tablets.

Example 11 is prepared in identical fashion to Example 10, except that 10 mg oxycodone HCl is included per tablet. The formulations for Examples 10 and 11 are set forth in Tables 13 and 14, respectively.

TABLE 13

| Formulation of Example 10 | | |
|---|---|---|
| Ingredient | mg/tablet | g/batch |
| Oxycodone hydrochloride | 4.0 | 32.0 |
| Lactose monohydrate | 30.0 | 240.5 |
| Hydroxyethylcellulose | 10.0 | 80.0 |
| Methacrylic acid copolymer | 30.0 | 240.0 |
| Cetostearyl alcohol | 30.0 | 240.0 |

TABLE 14

| Formulation of Example 11 | | |
|---|---|---|
| Ingredient | mg/tablet | g/batch |
| Oxycodone hydrochloride | 10.0 | 80.0 |
| Lactose monohydrate | 30.0 | 240.5 |
| Hydroxyethylcellulose | 10.0 | 80.0 |
| Methacrylic acid copolymer | 30.0 | 240.0 |
| Cetostearyl alcohol | 30.0 | 240.0 |

Next, dissolution studies were conducted on the tablets of Examples 6-11 using the USP basket method as described in the U.S. Pharmacopoeia XXII (1990). The speed was 100 rpm, the medium was simulated gastric fluid for the first hour followed by simulated intestinal fluid thereafter, at a temperature of 37° C. Results are given in Table 15.

TABLE 15

| | DISSOLUTION STUDIES OF EXAMPLES 6-11 | | | | | |
|---|---|---|---|---|---|---|
| Time | % Oxycodone Dissolved | | | | | |
| (hrs) | Ex. 6 | Ex. 7 | Ex. 8 | Ex. 9 | Ex. 10 | Ex. 11 |
| 1 | 23.3 | 25.5 | 28.1 | 29.3 | 31.3 | 40.9 |
| 2 | 35.6 | 37.5 | 41.5 | 43.2 | 44.9 | 55.6 |
| 4 | 52.9 | 56.4 | 61.2 | 63.6 | 62.1 | 74.2 |
| 8 | 75.3 | 79.2 | 83.7 | 88.0 | 82.0 | 93.9 |
| 12 | 90.7 | 94.5 | 95.2 | 100.0 | 91.4 | 100.0 |

EXAMPLES 12-14

Clinical Studies

In Examples 12 16, randomized crossover bioavailability studies were conducted employing the formulation of Examples 2 (organic manufacture) and 3 (aqueous manufacture).

In Example 12, a single dose fast/fed study was conducted on 24 subjects with oxycodone tablets prepared according to Example 3.

In Example 13, a steady-state study was conducted on 23 subjects after 12 hours with oxycodone tablets prepared according to Example 2, and compared to a 5 mg oxycodone immediate-release solution.

In Example 14, a single dose study was conducted on 8 subjects with 2×10 mg oxycodone tablets prepared according to Examples 2 and 3, respectively, compared to a 20 mg oxycodone immediate release solution.

In Example 15, a single dose study was conducted on 22 subjects using oxycodone tablets prepared according to Example 3, and compared to a 20mg oxycodone immediate release solution.

In Example 16, a 12 subject single-dose study was conducted using 3×10mg oxycodone tablets prepared according to Example 3, and compared to a 30mg oxycodone immediate release solution.

The results of Examples 12-16 are set forth in Table 16.

TABLE 16

| Example | Dosage | AUC ng/ml/hr | Cmax ng/ml | Tmax hr |
|---------|--------|--------------|------------|---------|
| 12 | 10 mg CR Fast | 63 | 6.1 | 3.8 |
|    | 10 mg CR Fed  | 68 | 7.1 | 3.6 |
| 13 | 5 mg IR q6h   | 121 | 17 | 1.2 |
|    | 10 mg CR q12h | 130 | 17 | 3.2 |
| 14 | 20 mg IR      | 164 | 24 | 2.2 |
|    | 2 × 10 mg CR  | 117 | 14 | 3.1 |
|    | 2 × 10 mg CR  | 129 | 14 | 2.6 |
| 15 | 20 mg IR      | 188 | 40 | 1.4 |
|    | 2 × 10 mg CR  | 197 | 18 | 2.6 |
| 16 | 30 mg IR      | 306 | 53 | 1.2 |
|    | 3 × 10 mg CR  | 350 | 35 | 2.6 |
|    | 30 mg CR      | 352 | 36 | 2.9 |

IR denotes immediate-release oxycodone solution.
CR denotes controlled-release tablets The examples provided above are not meant to be exclusive. Many other variations of the present invention would be obvious to those skilled in the art, and are contemplated to be within the scope of the appended claims.

What is claimed is:

1. A solid, controlled release, oral dosage form, the dosage form comprising an analgesically effective amount of oxycodone or a salt thereof in a matrix wherein the dissolution rate in vitro of the dosage form, when measured by the USP Paddle Method at 100 rpm at 900 ml aqueous buffer (pH between 1.6 and 7.2) at 37° C. is between 12.5% and 42.5% (by wt) oxycodone released after 1 hour, between 25% and 55% (by wt) oxycodone released after 2 hours, between 45% and 75% (by wt) oxycodone released after 4 hours and between 55% and 85% (by wt) oxycodone released after 6 hours, the in vitro release rate being independent of pH between pH 1.6 and 7.2 and chosen such that the peak plasma level of oxycodone obtained in vivo occurs between 2 and 4 hours after administration of the dosage form.

2. A dosage form according to claim 1 wherein the in vitro dissolution rate is between 17.5% and 38% (by wt) oxycodone released after 1 hour, between 30% and 50% (by wt) oxycodone released after 2 hours, between 50% and 70% (by wt) oxycodone released after 4 hours and between 60% and 80% (by wt) oxycodone released after 6 hours.

3. A dosage form according to claim 2 wherein the in vitro dissolution rate is between 17.5% and 32.5% (by wt) oxycodone released after 1 hour, between 35% and 45% (by wt) oxycodone released after 2 hours, between 55% and 65% (by wt) oxycodone released after 4 hours and between 65% and 75% (by wt) oxycodone released after 6 hours.

4. A dosage form according to claim 1 wherein the peak plasma level of oxycodone occurs between 2.25 and 3.75 hours after administration of the dosage form.

5. A dosage form according to claim 1 wherein a therapeutically effective amount of an oxycodone salt comprises between 2 and 50 mg of oxycodone hydrochloride.

6. A dosage form according to claim 1 wherein a therapeutically effective amount of an oxycodone salt comprises between 2 and 40 mg of oxycodone hydrochloride.

7. A solid controlled release oral dosage form, comprising an analgesically
   (a) effective amount of oxycodone or a salt thereof;
   (b) an effective amount of a controlled release matrix selected from the group consisting of hydrophilic polymers, hydrophobic polymers, digestible substituted or unsubstituted hydrocarbons having from about 98 to about 50 carbon atoms, and polyalkylene glycols; and
   (c) a suitable amount of a suitable pharmaceutical diluent, wherein said composition provides an in vitro dissolution rate of the dosage form when measured by the USP Paddle Method at 100 rpm at 900 ml aqueous buffer (pH between 1.6 and 7.2) at 37° C. is between 12.5% and 42.5% (by wt) oxycodone released after 1 hour, between 25% and 55% (by wt) oxycodone released after 2 hours, between 45% and 75% (by wt) oxycodone released after 4 hours and between 55% and 85% (by wt) oxycodone released after 6 hours, the in vitro release rate being independent of pH between pH 1.6 and 7.2 and chosen such that the peak plasma level of oxycodone obtained in vivo occurs between 2 and 4 hours after administration of the dosage form.

8. The controlled release composition of claim 7, wherein said controlled release matrix comprises an acrylic resin.

9. The controlled release composition of claim 8 which contains from about 2 to about 50 mg of oxycodone hydrochloride.

10. A solid controlled release oral dosage form, comprising
    (a) an analgesically effective amount of spheroids comprising oxycodone or a salt thereof and either a spheronising agent or an acrylic polymer or copolymer;
    (b) a film coating which controls the release of the oxycodone or oxycodone salt at a controlled rate in an aqueous medium, wherein said composition provides an in vitro dissolution rate of the dosage form; and
    (c) a suitable amount of a suitable pharmaceutical diluent, wherein said composition provides an in vitro dissolution rate of the dosage form when measured by the USP Paddle Method at 100 rpm at 900 ml aqueous buffer (pH between 1.6 and 7.2) at 37° C. between 12.5% and 42.5% (by wt) oxycodone released after 1 hour, between 25% and 55% (by wt) oxycodone released after 2 hours, between 45% and 75% (by wt) oxycodone released after 4 hours and between 55% and 85% (by wt) oxycodone released after 6 hours, the in vitro release rate being independent of pH between pH 1.6 and 7.2 and chosen such that the peak plasma level of oxycodone obtained in vivo occurs between 2 and 4 hours after administration of the dosage form.

11. The controlled release composition of claim 10, wherein said film coating comprises a water insoluble material selected from the group consisting of shellac or zein, a water insoluble cellulose, or a polymethacrylate.

12. The controlled release composition of claim 11, which contains from about 2 to about 50 mg of oxycodone hydrochloride.

13. A controlled release tablet for oral administration comprising an analgesically effective amount of oxycodone or an oxycodone salt dispersed in a controlled release matrix, comprising from about 5% to about 25% of an acrylic resin and from about 8% to about 40% of at least one aliphatic alcohol of 12-36 carbon atoms, by weight, wherein the dissolution rate in vitro of the dosage form, when measured by the USP Paddle Method at 100 rpm at 900 ml aqueous buffer (pH between 1.6 and 7.2) at 37° C. is between 12.5% and 42.5% (by wt) oxycodone released after 1 hour, between 25% and 55% (by wt) oxycodone released after 2 hours, between 45% and 75% (by wt) oxycodone released after 4 hours and between 55% and 85% (by wt) oxycodone released after 6 hours, the in vitro release rate being independent of pH between pH 1.6 and 7.2 and chosen such that the peak plasma level of oxycodone obtained in vivo occurs between 2 and 4 hours after administration of the dosage form.

14. A process for the preparation of a solid, controlled release, oral dosage form comprising incorporating an analgesically effective amount of oxycodone or a salt thereof in a controlled release matrix comprising from about 5% to about 25% of an acrylic resin and from about 8% to about 40% of at least one aliphatic alcohol of 12-36 carbon atoms, by weight, wherein the dissolution rate in vitro of the dosage form, when measured by the USP Paddle Method at 100 rpm in 900 ml aqueous buffer (pH between 1.6 and 7.2) at 37° C. is between 25% and 60% (by weight) oxycodone release after 1 hour, between 45% and 80% (by weight) oxycodone released after 2 hours, between 60% and 90% (by weight) oxycodone released after 3 hours, and between 70% and 100% (by weight) oxycodone released after 4 hours, the in vitro release rate being independent of pH between 1.6 and 7.2 and chosen such that the peak plasma level of oxycodone obtained in vivo occurs between 2 and 4 hours after administration of the dosage form.

15. The process of claim 14, further comprising wet granulating said oxycodone or a salt thereof with said acrylic resin in alcohol to form a granulate thereof;

adding said at least one aliphatic alcohol in a substantially liquid state to said granulate to obtain coated granules; and compressing and shaping the granules.

16. The process of claim 14, further comprising wet granulating said oxycodone or a salt thereof with said acrylic resin in water to form a granulate thereof;

adding said at least one aliphatic alcohol in a substantially liquid state to said granulate to obtain coated granules; and compressing and shaping the granules.

17. The process of claim 16, wherein a portion of said acrylic resin is dispersed in a suitable solvent and sprayed onto said granulate prior to adding said at least one aliphatic alcohol.

* * * * *

UNITED STATES PATENT AND TRADEMARK OFFICE
CERTIFICATE OF CORRECTION

PATENT NO. : 5,266,331

DATED : November 30, 1993

INVENTOR(S) : Benjamin Oshlack et al.

It is certified that error appears in the above-identified patent and that said Letters Patent is hereby corrected as shown below:

On the cover page, the portion reciting "The portion of the term of this patent subsequent to Feb. 5, 2008 has been disclaimed." should recite --The term of this patent shall not extend beyond the expiration date of Patent No. 4,990,341.--

Signed and Sealed this

Sixteenth Day of November, 1999

*Attest:*

Q. TODD DICKINSON

*Attesting Officer*     *Acting Commissioner of Patents and Trademarks*